(12) United States Patent
Wyeth et al.

(10) Patent No.: US 12,337,085 B2
(45) Date of Patent: Jun. 24, 2025

(54) USER INTERFACE MONITORING AND VERIFICATION THEREOF IN MEDICAL TREATMENT SYSTEMS

(71) Applicant: NxStage Medical, Inc., Lawrence, MA (US)

(72) Inventors: Mark T. Wyeth, Andover, MA (US); Gregory Yantz, Boxford, MA (US); Sarah-Paul McCarty, Reading, MA (US)

(73) Assignee: NxStage Medical, Inc., Lawrence, MA (US)

( * ) Notice: Subject to any disclaimer, the term of this patent is extended or adjusted under 35 U.S.C. 154(b) by 428 days.

(21) Appl. No.: 17/779,431

(22) PCT Filed: Nov. 19, 2020

(86) PCT No.: PCT/US2020/061277
§ 371 (c)(1),
(2) Date: May 24, 2022

(87) PCT Pub. No.: WO2021/108214
PCT Pub. Date: Jun. 3, 2021

(65) Prior Publication Data
US 2022/0409789 A1 Dec. 29, 2022

Related U.S. Application Data

(60) Provisional application No. 62/939,785, filed on Nov. 25, 2019.

(51) Int. Cl.
*A61M 1/16* (2006.01)
*A61M 1/28* (2006.01)
(Continued)

(52) U.S. Cl.
CPC ............ *A61M 1/1601* (2014.02); *A61M 1/28* (2013.01); *B01D 61/32* (2013.01);
(Continued)

(58) Field of Classification Search
CPC .. A61M 1/1601; A61M 1/28; A61M 2205/18; A61M 2205/27;
(Continued)

(56) References Cited

U.S. PATENT DOCUMENTS 6,406,426 B1 *   6/2002   Reuss ................ A61B 5/002
                                                           128/920
10,002,190 B2    6/2018   West
(Continued)

FOREIGN PATENT DOCUMENTS

CN     1227940 A  *  9/1999  ............... G06K 9/00
EP     0869433 A2 *  3/1998  ............... G06F 11/00
(Continued)

OTHER PUBLICATIONS

English translation of Patent Publication CN 1227940A, published Sep. 8, 1999. (Year: 1999).*
(Continued)

*Primary Examiner* — Joseph W Drodge
(74) *Attorney, Agent, or Firm* — Potomac Law Group, PLLC

(57) ABSTRACT

A medical treatment system is configured to output a predefined test pattern and to receive the signal by way of a microphone in order to test the volume and quality of the audio output in order to ensure the output audio signals effective to wake a sleeping patient. The failure of a processor to confirm the volume and fidelity of the audio output as well as the timeliness of the test pattern causes the processor to deny the resumption of a treatment and to generate an error signal.

10 Claims, 8 Drawing Sheets

(51) Int. Cl.
    *B01D 61/32*     (2006.01)
    *G06F 11/36*     (2025.01)
    *G06F 11/3668*   (2025.01)
    *G06K 5/00*      (2006.01)
    *G06V 10/00*     (2022.01)
(52) U.S. Cl.
    CPC ............ *G06F 11/3696* (2013.01); *G06K 5/00*
        (2013.01); *G06V 10/00* (2022.01); *A61M*
        *2205/18* (2013.01); *A61M 2205/27* (2013.01);
        *A61M 2205/3375* (2013.01); *A61M 2205/502*
        (2013.01); *A61M 2205/702* (2013.01)
(58) Field of Classification Search
    CPC .... A61M 2205/3375; A61M 2205/502; A61M
        2205/702; A61M 2205/186; A61M
        2205/3306; A61M 1/16; B01D 61/30;
        B01D 61/32; G06F 3/16; G06F 3/162;
        G06F 3/167; G06F 11/3688; G06F
        11/3696; G06F 11/3698; G06F 18/00;
        H04R 29/004; G06K 5/00; G06V 10/00;
        H03K 19/21
    See application file for complete search history.

(56) References Cited

U.S. PATENT DOCUMENTS

| | | | |
|---|---|---|---|
| 2009/0099867 A1 | 4/2009 | Newman | |
| 2009/0295591 A1* | 12/2009 | Bedingfield | H04R 29/001 |
| | | | 340/657 |
| 2012/0138533 A1 | 6/2012 | Curtis et al. | |
| 2013/0336814 A1* | 12/2013 | Kamen | A61M 5/16831 |
| | | | 417/302 |
| 2016/0077955 A1* | 3/2016 | Werghis | G06F 3/0481 |
| | | | 715/762 |
| 2017/0056604 A1* | 3/2017 | Cowan | A61M 5/14546 |
| 2017/0065757 A1* | 3/2017 | Tanenbaum | A61M 1/1601 |
| 2017/0300643 A1* | 10/2017 | Bezark | G06Q 40/08 |
| 2018/0036466 A1 | 2/2018 | Tarn et al. | |
| 2018/0075203 A1 | 3/2018 | West et al. | |
| 2019/0102072 A1* | 4/2019 | Strinden | G05B 19/409 |
| 2019/0209764 A1* | 7/2019 | Buraczenski | G16H 40/63 |
| 2019/0382336 A1* | 12/2019 | Lowther | C07D 233/90 |
| 2020/0065184 A1* | 2/2020 | Channappagoudar | G06N 7/01 |

FOREIGN PATENT DOCUMENTS

| | | |
|---|---|---|
| WO | 03058567 A2 | 7/2003 |
| WO | 2018045102 A1 | 3/2018 |

OTHER PUBLICATIONS

International Search Report and Written Opinion mailed Feb. 9, 2021 for International Patent Application No. PCT/US2020/061277.

Extended European Search Report dated Oct. 19, 2023 for European Patent Application No. 20891859.9.

* cited by examiner

USER INTERFACE MONITORING AND VERIFICATION THEREOF IN MEDICAL TREATMENT SYSTEMS

CROSS-REFERENCE TO RELATED APPLICATIONS

This application is a U.S. national stage filing under 35 U.S.C. § 371 of International Application No. PCT/US2020/061277, filed Nov. 19, 2020, which claims priority to and the benefit of U.S. Provisional Patent Application No. 62/939,785 filed Nov. 25, 2019, all of which are hereby incorporated by reference in their entireties.

BACKGROUND

The present invention relates generally to medical treatments performed with life-assisting and life-saving machines such as those used for dialysis, and more specifically to the transmission and verification of output and/or expected output which is necessary to treatment.

The adequate delivery of treatment, whether according to hemodialysis, hemofiltration or peritoneal dialysis, for example and as described in WO 2018/045102 (incorporated by reference in its entirety herein), must be ensured in order to accomplish the intended effect of the treatment. Assessment of that effect is dependent on receiving machine output which is correct. Examples of such parameters include machine errors, treatment errors, alarms, etc.

Conditions including machine operating conditions and treatment conditions may be detected by one or more sensors that each convey sensor information in a form receivable by a controller that is in communication with a user interface enabled to both inform the machine operator of the output, receive input from the machine operator in response to the output, and to take specific actions such as halting a treatment. The controller may be used to regulate one or more processes of devices in communication with the sensors and the treatment in general through interaction with the machine operator via the user interface. That is, the user interface must be able to make the output properly available to the machine operator for assessment.

As will be understood, the output is generally one or more forms of data which the operator can assess by comparison to a given other one or more data of the output, or to personal knowledge of baselines and ranges for the data enabling correlation to a standard. For example, comparison of the output to the standard may prescribe that the operator use the user interface to cause the machine to adjust a dialysate infusion level or halt the treatment if the standard is violated.

Alternatively, the machine itself may be embodied to conduct the aforementioned comparisons and automatically carry out an appropriate functionality according to the output.

SUMMARY

During the administration of treatment a machine controller may detect incorrect output of information to an operator and take corrective action or output an alarm or other indicator of a fault. Still further, a machine controller may provide verification of the output during start-up, maintenance, or prior to or during a course of a treatment.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1:
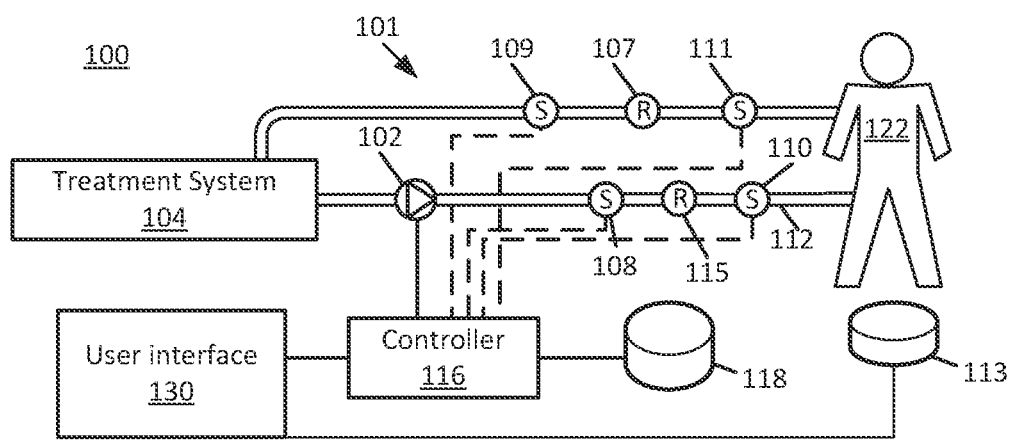
FIG. 1 is a schematic illustration of a dialysis machine, according to embodiments of the disclosed subject matter.

A generalized dialysis treatment machine 100 is shown in FIG. 1, and includes a treatment system 104, which may include a blood treatment device that transfers a fluid, such as blood, from and to a patient 122. The system may also represent a peritoneal dialysis machine that transfers peritoneal dialysate to the patient and withdraws peritoneal dialysate from the patient 122. Fluid is conveyed via a fluid circuit 101 that includes lines 112 that engage, or expose contents to, one or more sensors 109, 111, 108 and 112. Sensor signals of sensors 109, 111, 108 and 112 are conveyed to a controller 116 which may control pumps such as pump 102, and other pumps not shown, as required. Sensor signals of sensors 109, 111, 108 and 112 may also represent sensor information that may be used by controller 116 to cause the generation of various output, including the display, enunciation, and/or recording of a treatment alarm and related patient status/data, transmission of the output to a healthcare provider such as the operator of the computer system discussed below, and control delivery of a medicine to the patient 122 (e.g., by controlling an IV or a substance added to the fluid in lines 112).

Fluid may be conveyed through flow restrictions 107, 115 to facilitate measurement of a parameter of the fluid, for example, a viscosity of a respective one of blood or peritoneal dialysate in various embodiments. However, any other known means of measuring viscosity may be used in alternative embodiments, such as any known viscometer or rheometer or by using an optical technique. Captured measurements may be stored by the controller 116 on a non-volatile data store 118 that resides locally or in the cloud.

System 104 may alternatively or additionally include a weight scale 113 that provides a signal indicative of the weight of the patient 122, and the controller 116 may use such signal, instead of, or in combination with, signals produced by the one or more sensors 109, 111, 108, 110, to implement any functionality described herein with reference to a treatment of the patient 122.

Figure 2:
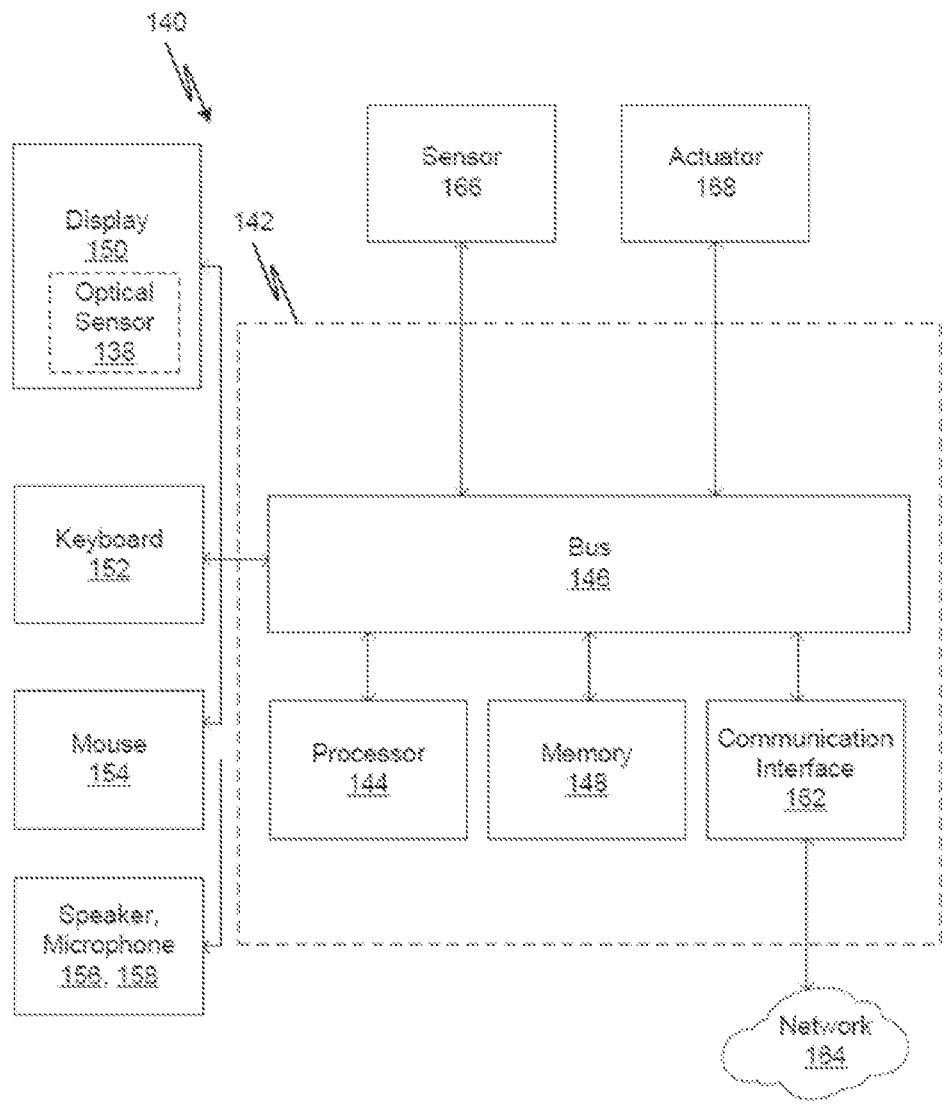
FIG. 2 is a block diagram of an example computer system, according to embodiments of the disclosed subject matter.

FIG. 2 is a block diagram of an example computer system 140 according to an embodiment. In various embodiments, all or parts of system 140 may be operatively coupled with or included in a medical treatment device/system 100, such as a renal replacement therapy system of the type described above. In these embodiments, all or parts of system 140 may provide the functionality of the controller 116. In some embodiments, all or parts of system 140 may be implemented as a distributed system, for example, as a cloud-based system.

System 140 includes a computer 142 such as a personal computer or workstation or other such computing system that includes a processor 144. However, alternative embodiments may implement more than one processor and/or one or more microprocessors, microcontroller devices, or control logic including integrated circuits such as ASIC.

Computer 142 further includes a bus 146 that provides communication functionality among various modules of computer 142. For example, bus 146 may allow for communicating information/data between processor 144 and a memory 148 of computer 142 so that processor 144 may retrieve stored data from memory 148 and/or execute instructions stored on memory 148. In embodiments, such instructions may be compiled from source code/objects provided in accordance with a programming language such as Java, C++, C#, .net, Visual Basic™, LabVIEW, or another structured or object-oriented programming language. In embodiments, the instructions include software modules that, when executed by processor 144, provide renal replacement therapy functionality according to any of the embodiments disclosed herein.

Memory 148 may include any volatile or non-volatile computer-readable memory that can be read by computer 142. For example, memory 148 may include a non-transitory computer-readable medium such as ROM, PROM, EEPROM, RAM, flash memory, disk drive, etc. Memory 148 may be a removable or non-removable medium.

Bus 146 may further allow for communication between computer 142 and a display 150, a keyboard 152, a mouse 154, a speaker 156, a microphone 158, and a camera 160 each providing respective functionality in accordance with various embodiments disclosed herein, for example, for configuring a treatment for the patient 122 and monitoring the patient 122 during that treatment.

Computer 142 may also implement a communication interface 162 to communicate with a network 164 to provide any functionality disclosed herein, for example, for notifying an operator (i.e., healthcare professional) of a treatment alarm and/or receiving instructions from the healthcare professional, reporting patient/device conditions in a distributed system for training a machine learning algorithm, logging data to a remote repository, etc. Communication interface 162 may be any such interface known in the art to provide wireless and/or wired communication, such as a network card or a modem.

Bus 146 may further allow for communication with a sensor 166 and/or an actuator 168, each providing respective functionality in accordance with various embodiments disclosed herein, for example, for measuring signals indicative of a patient/device condition and for controlling the operation of the device accordingly. For example, sensor 166 may provide a signal indicative of a viscosity of a fluid in a fluid circuit in a renal replacement therapy device, and actuator 168 may operate a pump that controls the flow of the fluid responsively to the signals of sensor 166.

Figure 3:
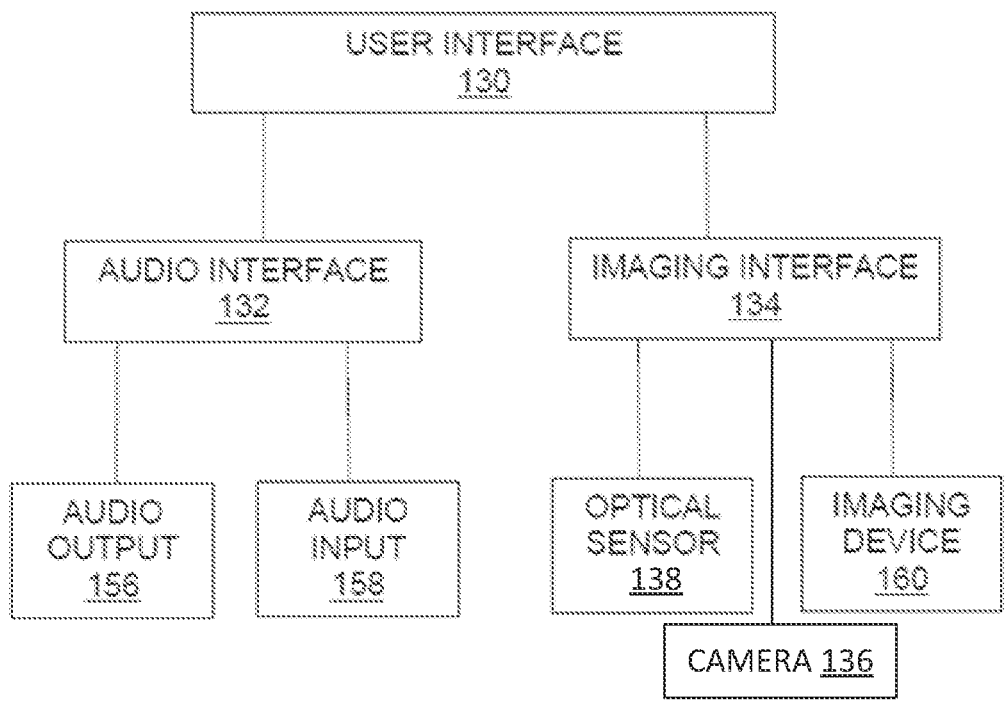
FIG. 3 is a block diagram of an example user interface according to FIGS. 1 and 2.

With reference to FIGS. 1, 2, and 3, treatment machine 100 further defines a user interface 130, as shown in FIG. 1, for interacting with the treatment device (e.g., a dialysis machine) 100 of FIG. 1 and computer system 140. The user interface 130 defines an audio interface 132 and an imaging interface 134. Audio interface 132 includes an output such as the speaker 156, and an input such as the microphone 158. In embodiments, the speaker 156 and microphone 158 may also be stand-alone devices. Imaging interface 134 includes an optical sensor 138 and an imaging device 160 such as a camera. The imaging interface also includes an imaging output such as a display 150. In embodiments, the optical sensor 138 may be embedded within the display 150 as shown in FIG. 2 and the imaging device 160 may be a camera aimed at and focused on the display 150.

Throughout treatment of a patient 122, critical messages and audio output may be generated through the user interface 130. The output may include alarms, instructions for recovery, and other output. The output may also include general information about the patient parameters or treatment system parameters.

The audio interface 132 is configured to generate output, such as sounding of an alarm if one or more levels or conditions of parameters of the treatment runs outside of an expected range of parameters. To test alarm systems, during a start-up operation or at any other time such as during maintenance or at the command of a user through a user interface, a test signal may be output through the audio output 156 (e.g., a speaker or other audibly perceivable transducer). Additionally, and similarly, a test pattern may be generated and output on the display 150. The output is received by a suitable device such as a light sensor, camera, or microphone and evaluated for its fidelity.

Note, an audio input (e.g., microphone) 158 may provide additional functions besides receiving the test signal output such as receiving input from an operator such as spoken commands. By processing and analyzing the audio from the speaker, the speaker output may be evaluated for irregularities in power spectrum, audio level, or other characteristics which may indicate improper functioning of the speaker 156 and/or one or more components of the machine 100 and/or computer system 140.

In embodiments and by way of example, a power spectrum of the audio output may be compared to a template stored by the system 140 to evaluate the fidelity and volume of the audio output. For example the power spectrum may indicate a faulty speaker by revealing a buzz, for example, or low audio power output (sound pressure).

Likewise, user interface 130 may be configured to produce a test pattern output in the form of a displayed/visible image. An imaging interface 134 may generate the displayed image. In embodiments, the optical sensor 138 can capture a brightness of the display and timing of the output. Camera 160 may be focused on the display 150 and may capture images that are then compared to templates to determine whether the display is working correctly. The image may be subjected to image processing and classified in other ways. For example, a difference image may be obtained and compared to an expected difference image between an accurate rendering and the expected image output and the detected difference image. In order to assess functionality of the display of an output, for example an alarm, one or more of the optical sensor 138 capture and camera 136 capture are relayed to processor 144, and system 140 more generally.

In embodiments, system 140 may include software and/or hardware enabling alternate paths of communication of an output alarm when, during a treatment, a selected interface (e.g., audio interface 132 or display 150) are identified as non-functional or have inadequate. In embodiments, such alternate paths may include the following non-limiting examples such as paging, email, and text messaging. Throughout, system 140 may be configured to provide the above-discussed alarm and test and verify the adequacy of the alarm using the audio interface 132, display 150 and imaging interface 134, either alone or in combination.

Features of the disclosed embodiments may be combined, rearranged, omitted, etc., within the scope of the invention to produce additional embodiments. Furthermore, certain features may sometimes be used to advantage without a corresponding use of other features.

Figure 4:
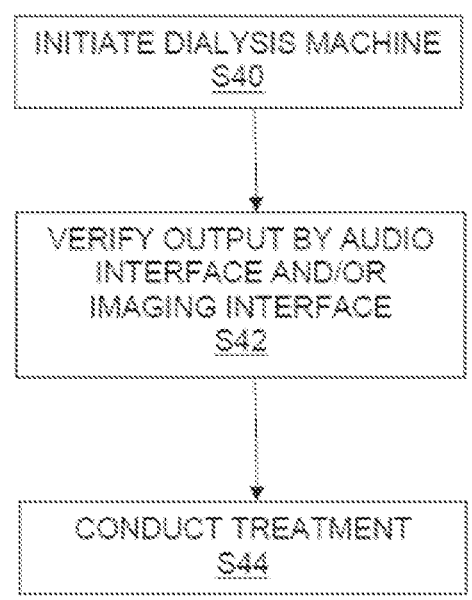
FIG. 4 is an example of initiation of the dialysis machine of FIG. 1 in conjunction with initiation of the computer system of FIG. 2, according to embodiments of the disclosed subject matter.

Referring now to FIG. 4, there is shown a process for initiating (i.e., powering on) the treatment machine 100 of FIG. 1 and computer system 140 in conjunction therewith. At S40, each of the treatment machine 100 and computer system 140 are powered to activate their constituent components before beginning a treatment of the patient 122. In embodiments, one or more of the audio interface 132 may be caused, via processor 144, to output through speaker 156 a test audio sequence, for example, a readiness tone, a coded signal, or a beep forming part of an overall startup indication triggered by each of the treatment machine 100 and computer system 140 more generally. Alternatively synthetic speech or a recording may be output. As such, the operator is made aware of the readiness state of the audio interface 132. The audio is a test signal selected to be distinguishable from background sounds. Alternatively, or in addition, an image output may be generated on the display 150.

To distinguish background sounds and noises, the test audio output may have a distinctive audio signature such as a timed series of chirps or a unique frequency pattern that makes it stand out from the background and gives it uniqueness relative to other machines in the vicinity of the treatment machine. For example, a sequence of chirps might be separated in time with a variety of different silent gaps between them thereby forming a unique output signal. A unique code may be represented as a unique set of frequency hops like a bird song. Another example may be a unique sound spectral density function with peaks and troughs that are unique to the particular machine. The audio pattern may include a sound intensity level. In other words, the test pattern may be found acceptable by the system as long as the sound level is high enough to be audible. Note that the test signal maybe required to satisfy other criteria such as an audio spectrum that matches one provided by a template. This might indicate when a speaker is not functioning property such as one that produces a buzz.

In embodiments at S42, an automatic detection of errors in output may be obtained using the processes described herein and, by way of example, listed in Table 1 below. So the startup sounds and visual output may serve to confirm correct operation of the treatment system output components and the devices that generate the output. That is, the processor may self-determine if correct output is generated by comparing to expected output.

Figure 5:
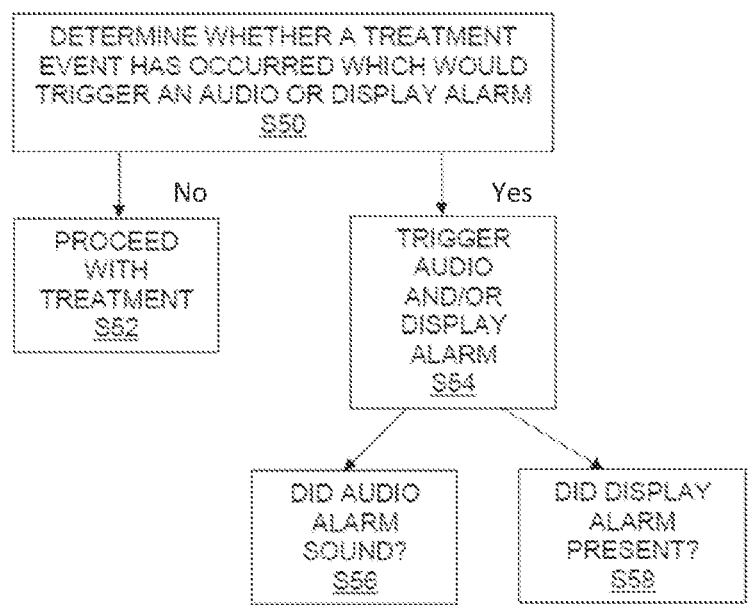
FIG. 5 is an example method of determining functionality of various alarm systems that may be invoked by the dialysis machine of FIG. 1, according to embodiments of the disclosed subject matter.

Referring now to FIG. 5, once treatment has begun, treatment machine 100 may, in embodiments, conduct ongoing monitoring for a treatment event indicative of an alarm condition S50. This way, proper functioning of the treatment machine 100 and/or computer system 140 will trigger production of an alarm in regard to an occurrence of the treatment event. As described above, such improper or unintended treatment refers to any situation in which either the treatment machine causes the performance of the treatment to result in an alarm signaling that one or more parameters or conditions of the treatment negate or deviate from one or more standards for the treatment. If no treatment event indicative of improper or unintended treatment is detected, treatment will proceed as indicated at S52. At S54, however, detection of such an event will cause treatment machine 100 and/or computer system 140 to trigger an alarm via speaker 156 or by means of a display 150 showing an image or both. At S50, the fidelity of the alarm output is evaluated and if correct, recover instructions corresponding to the alarm are generated. If the fidelity of the alarm is determined to be incorrect, a maintenance alarm is generated at S54. At S56, a verification is made to confirm whether the audio alarm did, in fact, sound. At S58, a verification is made to confirm whether a visual alarm did, in fact, present on the graphical output (e.g., on the display 150).

Figure 6:
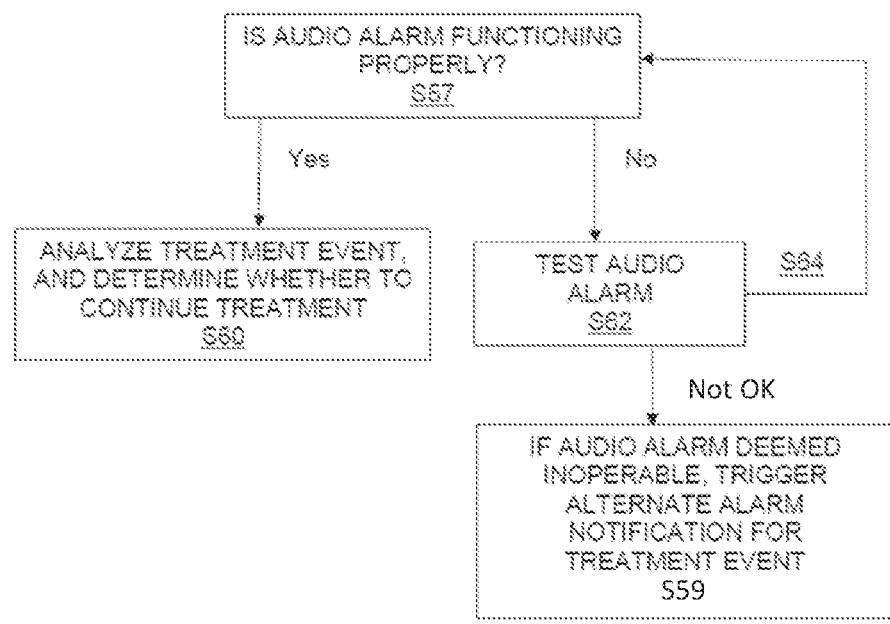
FIG. 6 illustrates a method for a start-up protocol according to embodiments of the disclosed subject matter.

Additional exemplary details of S56 are illustrated in FIG. 6. At S57, a determination is made whether the audio alarm is functioning properly. For example, an input signal to the speaker 156 may be compared to an output signal of the microphone 158. The two signals may be first rectified and then subtracted from each other, to effectively perform an absolute value operation of each before the subtraction. The remaining signal will then be compared to a threshold to determine whether the two signals were sufficiently similar, to deem the audio alarm to be functioning properly.

If the audio alarm is functioning properly, the process continues at S60, where an analysis is made to determine whether the continue the medical treatment despite the alarm condition.

If a determination is made that the audio alarm is not functioning properly at S57, the process continues to S62 where further tests of the audio alarm are conducted. For example, a special test signal can be input to the audio output device and any audio output may be monitored by the audio input device. The test signal can be a sweep function in a range of frequencies that are inaudible to a human (i.e., above 20 kHz), to thereby avoid disturbing the patient. Alternatively or additionally, a full spectrum sweep may be performed to determine whether the audio output device has some physical defect that might be preventing the output of certain frequencies. If the test of the audio alarm at S62 is successful, the processing continues at S64 to S57.

If the audio alarm is deemed to be inoperable at S62, the process continues to S59, where an alternate alarm is triggered, such as a visual alarm and/or transmitting electronic signals or radio signals to an external device or a server.

Figure 7:
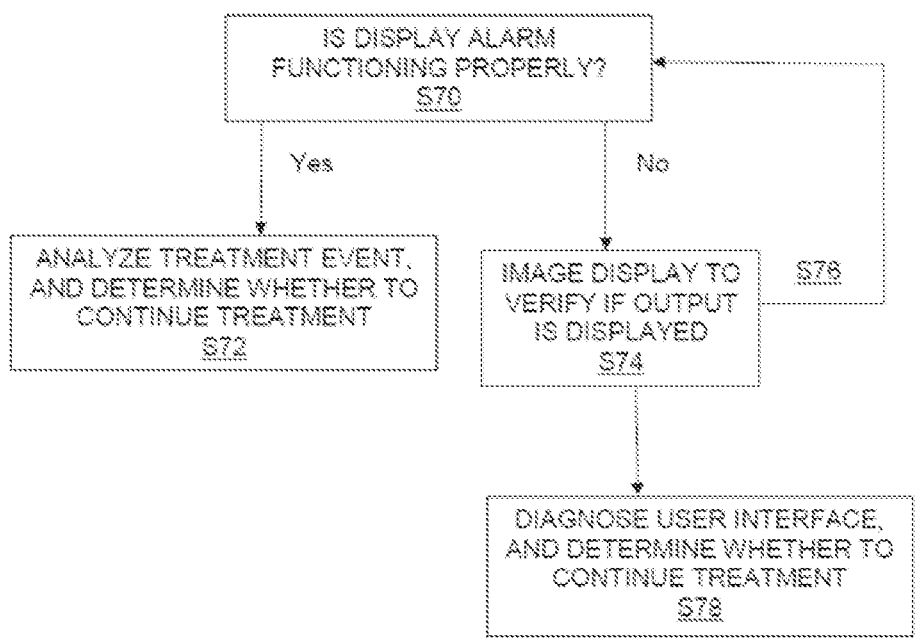
FIG. 7 shows a control breakdown according to the method of FIG. 6 according to embodiments of the disclosed subject matter.

FIG. 7 illustrates exemplary details of S58 from FIG. 5. At S58, a verification is made to confirm whether a visual alarm did, in fact, present on the graphical output (e.g., on the display 150). This verification can be, for example, be made by a camera aimed at the display and recording an image that is shown on the display, and comparing the pixel values of the recorded image against the input to the display, as would be done at S74. If the pixel values are within some predetermined threshold, it is determined that the display did correctly generate a visual alarm at S76.

If the display alarm is functioning properly at S70, the process continues at S72 to determine whether to continue the treatment despite the alarm condition. If at S74 it is determined that the display is not functioning properly, the graphical user interface is diagnosed at S78 and a determination is made whether to continue treatment at S78. For example, a synthesized voice can announce the alarm condition (e.g., "patient line may be occluded") and also may announce possible steps to take, such as pressing a button to continue treatment, or avoiding pressing the button and allowing the treatment to end automatically.

Figure 8:
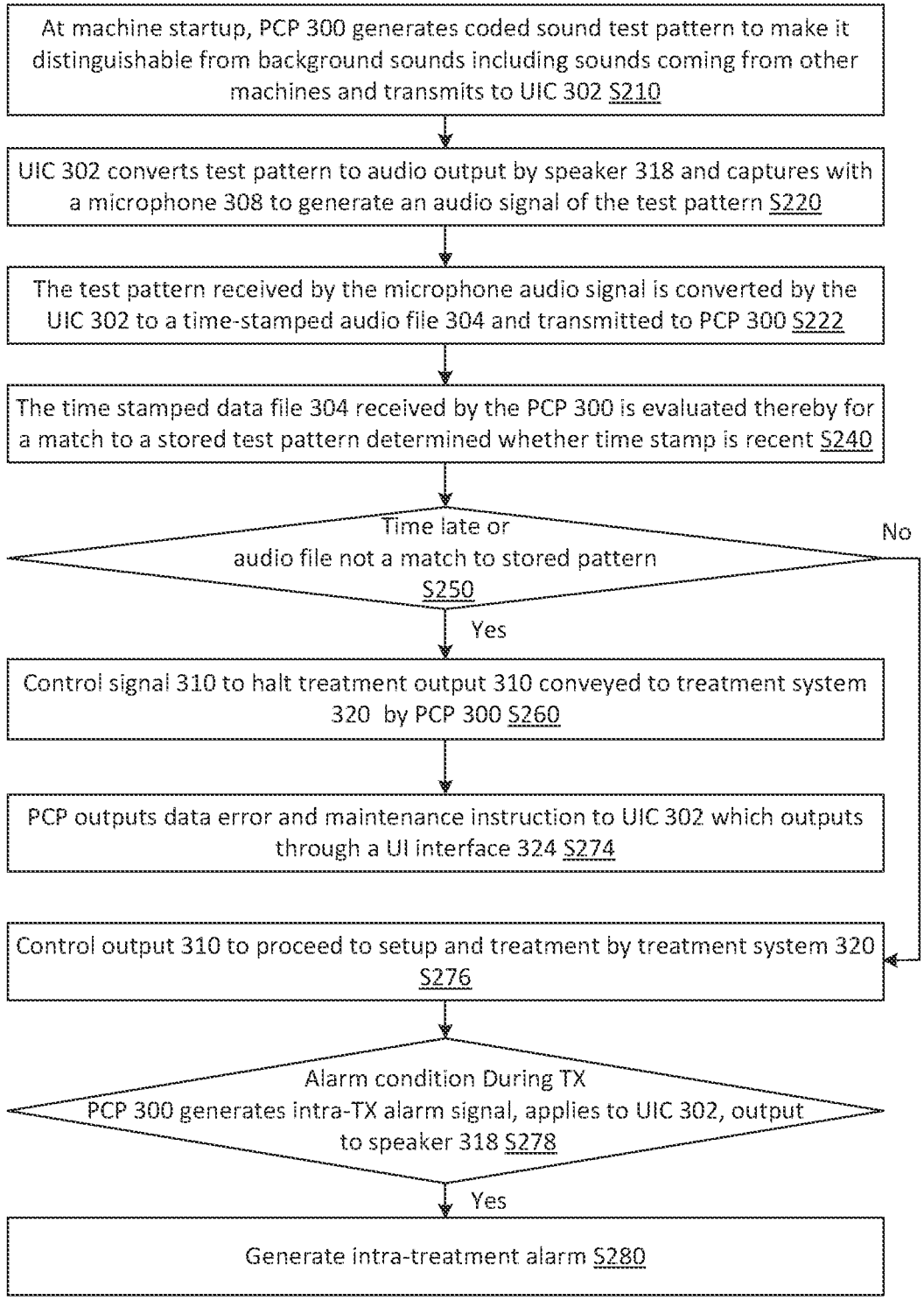
FIGS. 8 and 9 show a procedure and processor configuration for verifying the output of an audio alarm according to embodiments of the disclosed subject matter.
Figure 9:
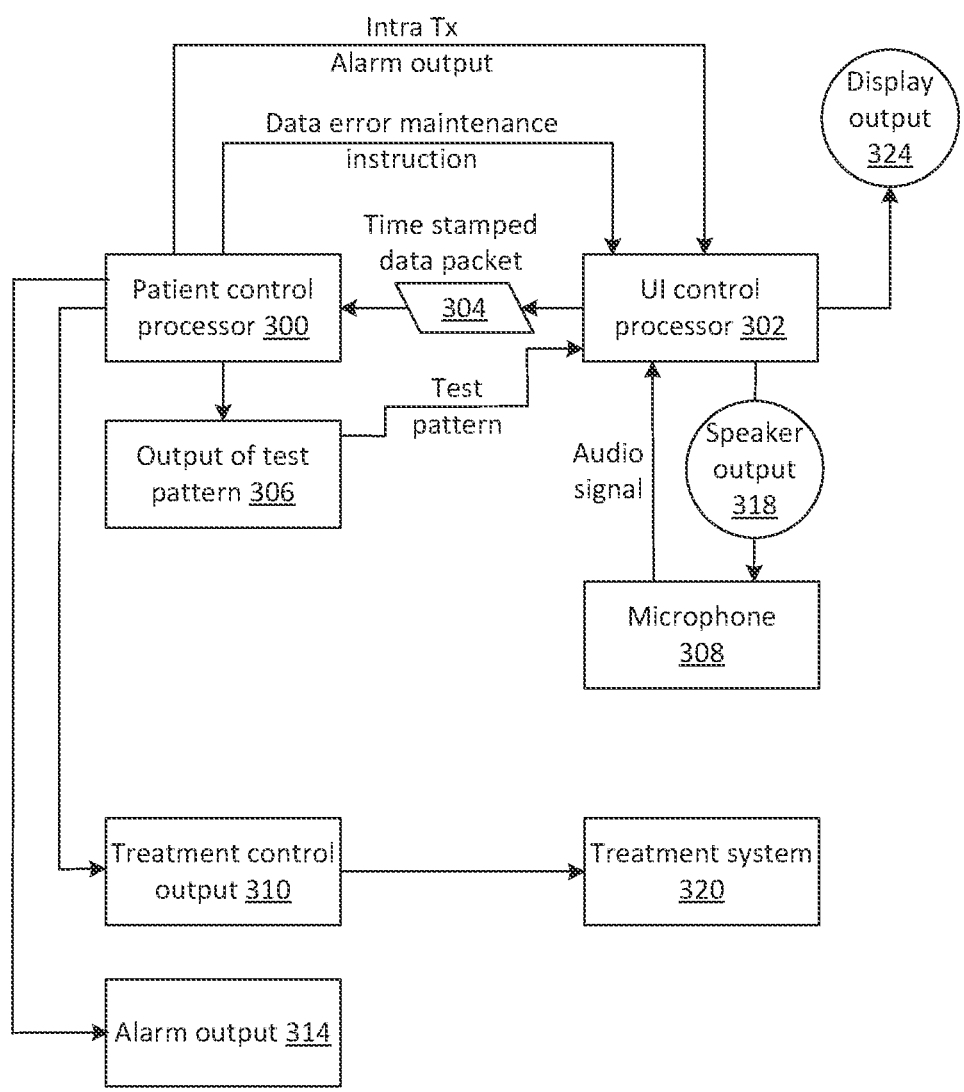

Referring now to FIGS. 8-9, an embodiment of a method of testing an audio output of an alarm system and for controlling a treatment device 320 is shown. At S210, upon treatment system 320 startup, an audio output alarm, which is important to safety because it may be relied upon to alert a patient who is at risk if a malfunction arises. Since a patient is generally sleeping when undergoing treatment, an audio alarm may need to wake the patient in the event of a malfunction that requires his attention. At treatment system 320 startup, a patient control processor 300 generates an audio test pattern 306 that is selected for its ability to be distinguished from background sounds including noise and other machine alarms and test patterns, for example as may occur in a dialysis treatment clinic. For example, the test pattern 306 may have a coded pattern that is unique to the particular treatment system 320 to which it relates. The function provided by the pattern is to allow the system to determine if the audio output is correct and to ensure that the audio output is distinguishable from background sounds. Moreover, the test pattern 306 may be different from an alarm output 314, to avoid unintentionally making the patient think that an actual alarm condition is present.

The test pattern is applied to a user interface controller 302 which converts the test pattern S220 to an audio output through a speaker 318 whose output is picked up by a microphone 308 and converted to an analog signal which is sampled and converted by the user interface controller 302 to a digital audio file at S222. The audio file 304 is time-stamped by the user interface controller 302 and transmitted to the patient control processor 300. The file is received at S240 by the patient control processor 300 at S240. The patient control processor determines at S250 whether the time stamp is recent and whether there is a good match between a stored pattern and the pattern received through the microphone 308.

At S260, if the audio file is a poor match (including sound levels and pattern) or the time stamp indicates the file is not recent, then at S260, a control signal 310 is generated to halt the treatment and conveyed to the treatment system 320. At S274, a data error maintenance instruction is transmitted to the user interface controller 302 and output on a display output 324. If the time stamp and pattern of the audio test signal are correct, then at S276, the patient control processor 300 generates treatment control output 310 to permit the treatment system 320 to set up and perform a treatment. If, during a treatment, an alarm condition arises that requires operator attention, at S278, then at S280, an intra-treatment alarm is output from the patient control processor 300 to the user interface controller 302 which generates an audio output through the speaker 318 alerting the operator to the alarm condition.

In the method, two processors are relied upon for testing the alarm output 314, one for evaluating the output integrity and one for outputting the alarm itself. Both processors can be controlled by software but one of the processors may be programmed to a lower level standard, namely, the user interface controller. Note that the two processors may be replaced by a single processor running separate programs with each program corresponding to respective function of the two processors.

In embodiments, treatment machine 100 and/or computer system 140 may be configured to provide an alarm for a treatment event via audio interface 132, display 150 and imaging interface 134 and the discussed alternative paths of notification, either singularly or in combination. When provided singularly, expected output by each of audio interface 132 and display 150 and imaging interface 134 may be compared to standardized versions of a respective alarm stored by treatment machine 100 and computer system 140 in their respective memories 118, 148. In other words, iterative testing as contemplated in FIGS. 6 and 7 will proceed in the absence of operability of the other of the audio interface 132 and display 150 and imaging interface 134.

In embodiments, it is to be understood that such iterative testing may be triggered by initiation of the treatment machine 100 and/or computer system 140 and throughout treatment of the patient until completion thereof and/or shutdown of one or more of the treatment machine 100 and computer system 140. In all instances, it will be understood that the above-discussed output/alarm has been delivered to the operator of the treatment machine 100 in the absence of a determination that the audio interface 132 or display 150 and imaging interface 134 are inoperable to produce the output.

In embodiments, the treatment machine 100 may go through a routine of self-tests including test display and audio outputs that are evaluated in the various ways described herein.

Table 1 below summarizes the various possible conditions recognized and responded to by the foregoing apparatuses. The row indices correspond to the paragraph numbering below.

1. Audio speech is detected by a microphone and an average power level of the sound detected and compared to a threshold expected value. The microphone may be suitably placed so as to detect background noise as well as the sound of the audio speech from a speaker. The sound level may be recognized by comparison to a predefined magnitude and specifically, the sound level during output and between output instances may be compared to subtract background noise levels to determine if the power level is sufficiently higher than background to be understood. The volume may be adjusted responsively to a result of the comparison.

2. Audio speech is detected by a microphone and an average power level of the sound detected and compared to a threshold expected value. The microphone may be suitably placed so as to detect background noise as well as the sound of the audio speech from a speaker. The sound level may be recognized by comparison to a predefined magnitude and specifically, the sound level during output and between output instances may be compared to subtract background noise levels to determine if the power level is sufficiently higher than background to be understood. If a failure to meet predefined sound levels is established by the controller, an alternate alarm may be output and recovery procedures performed. For example, the system may halt treatment temporarily and output instructions for reestablishing treatment or correcting a problem with the system.

3. Audio speech is detected by a microphone and a temporal pattern is detected and converted to a power spectral density function in order to detect sound quality or a normal speech audio pattern. The microphone may be suitably placed so as to detect background noise as well as the sound of the audio speech from a speaker. The spectrum with background noise and without may be compared to determine if audio output is comprehensible. If a failure to meet predefined audio quality levels is established by the controller, an alternate alarm may be output and recovery procedures performed. For example, the system may halt treatment temporarily and output instructions for reestablishing treatment or correcting a problem with the system.
4. Audio speech is detected by a microphone and a temporal pattern is detected and converted to a power spectral density function in order to detect sound quality or a normal speech audio pattern. The audio may be applied to a processor running a speech to text algorithm and a text output generated and matched to predefined text representing the expected output. If a failure to meet a predefined match is established by the controller, an alternate alarm may be output and recovery procedures performed. For example, the system may halt treatment temporarily and output instructions for reestablishing treatment or correcting a problem with the system.
5. Output from an audio annunciator is directly detected by a microphone and sound levels or patterns detected and the alarm output adjusted accordingly. The microphone may be suitably placed so as to detect background noise as well as the sound of the audio speech from a speaker. The sound level may be recognized by comparison to a predefined magnitude and specifically, the sound level during output and between output instances may be compared to subtract background noise levels to determine if the power level is sufficiently higher than background to be understood. The volume may be adjusted responsively to a result of the comparison.
6. Output from an audio annunciator is directly detected by a microphone and sound levels or patterns detected and the alarm output adjusted accordingly. The microphone may be suitably placed so as to detect background noise as well as the sound of the audio speech from a speaker. The sound level may be recognized by comparison to a predefined magnitude and specifically, the sound level during output and between output instances may be compared to subtract background noise levels to determine if the power level is sufficiently higher than background to be understood. If a failure to meet a predefined match is established by the controller, an alternate alarm may be output and recovery procedures performed. For example, the system may halt treatment temporarily and output instructions for reestablishing treatment or correcting a problem with the system.
7. Output from a visual annunciator such as a flashing or steady lamp is directly detected by a light sensor and luminance levels or patterns detected and the alarm output adjusted accordingly. The light level may be recognized by comparison to a predefined magnitude and specifically. If the luminance is insufficient, the light intensity may be adjusted responsively to a result of a comparison. This may automatically adjust for background light by direct ambient light detection a well.
8. Output from a visual annunciator such as a flashing or steady directly detected by a light sensor and luminance levels or patterns detected and the alarm output adjusted accordingly. The light level may be recognized by comparison to a predefined magnitude and specifically. If a failure to meet a predefined match is established by the controller, an alternate alarm may be output and recovery procedures performed. For example, the system may halt treatment temporarily and output instructions for reestablishing treatment or correcting a problem with the system.
9. A visual output such as steady or moving image may be output on a user interface display and the intensity and/or color may be detected by a light sensor. The intensity or color may be thresholded and compared with an expected value of luminance or chrominance. The output intensity may be adjusted responsively to the detected comparison.
10. A visual output such as steady or moving image may be output on a user interface display and the intensity and/or color may be detected by a light sensor. The intensity or color may be thresholded and compared with an expected value of luminance or chrominance. An alternative output may be generated responsively to the comparison. Recovery procedures performed. For example, the system may halt treatment temporarily and output instructions for reestablishing treatment or correcting a problem with the system.
11. A visual output such as steady or moving image may be output on a user interface display and the intensity and/or color may be detected by a light sensor. The time-ordered intensity or color may be thresholded and compared with an expected sequence of luminance or chrominance values. An alternative output may be generated responsively to the comparison. Recovery procedures performed. For example, the system may halt treatment temporarily and output instructions for reestablishing treatment or correcting a problem with the system.
12. A visual (video or image) output is generated and imaged by a camera. The pre-processing may include planar projection correction such as keystone correction such that the camera may be located immediately below or to the side or above the display. The image may be differenced with an expected output to determine a match. If the match fails to meet a predetermined threshold, an alternative output may be generated responsively to the comparison. Recovery procedures performed. For example, the system may halt treatment temporarily and output instructions for reestablishing treatment or correcting a problem with the system.
13. A visual (video or image) text output is generated and imaged by a camera. The pre-processing may include planar projection correction such as keystone correction such that the camera may be located immediately below or to the side or above the display. The image may be subjected to optical character recognition algorithm and the text output may be compared to expected text to determine a match. If the match fails to meet a predetermined threshold, an alternative output may be generated responsively to the comparison. Recovery procedures performed. For example, the system may halt treatment temporarily and output instructions for reestablishing treatment or correcting a problem with the system.

TABLE 1

Examples of processing, recognition, and response of system

| Idx | Output | Detected | Sensor | Pre-processing | Recognition | Response |
|---|---|---|---|---|---|---|
| 1 | Audio speech | Sound level | Microphone | Power threshold | Sound level | Adjust volume and repeat |
| 2 | Audio speech | Sound level | Microphone | Power threshold | Sound level | Alt alarm output - halt/recover |
| 3 | Audio speech | Sound pattern | Microphone | PSD | Audio quality | Alt alarm output - halt/recover |
| 4 | Audio speech | Sound pattern | Microphone | Speech to text | Match | Alt alarm output - halt/recover |
| 5 | Audio annunciator | Sound level | Microphone | Power threshold | Sound level | Adjust volume and repeat |
| 6 | Audio annunciator | Sound level | Microphone | Power threshold | Sound level | Alt alarm output - halt/recover |
| 7 | Visual annunciator | Intensity | Light sensor | Power threshold | Luminance | Adjust output |
| 8 | Visual annunciator | Intensity | Light sensor | Power threshold | Luminance | Alt alarm output - halt/recover |
| 9 | Visual image | Intensity/color | Light sensor | Threshold | Luminance or chrominance | Adjust output |
| 10 | Visual image | Intensity/color | Light sensor | Threshold | Luminance or chrominance | Alt alarm output - halt/recover |
| 11 | Visual image | Intensity/color | Light sensor | Time profile | Temporal pattern | Alt alarm output - halt/recover |
| 12 | Visual image | Image | Camera | Difference image | Match pattern | Alt alarm output - halt/recover |
| 13 | Visual image | Image | Camera | OCR | Match text | Alt alarm output - halt/recover |

One general aspect of the present disclosure includes a dialysis system for delivering treatment to a patient. The dialysis system also includes a user interface control processor configured to receive a test pattern from a patient control processor and to output on an audio output device. The system also includes a microphone positioned to receive audio output from said audio output device and to generate an audio signal that is interpretable by the patient control processor and which audio signal can be compared to a predefined pattern to determine whether it matches the pattern or not. The system also includes the patient control processor being configured to output an error signal if the audio signal doesn't match the predefined pattern. Other embodiments of this aspect include corresponding computer systems, apparatus, and computer programs recorded on one or more computer storage devices, each configured to perform the actions of the methods.

Implementations may include one or more of the following features. The system where: the user interface is configured to generate a time indication in relation to the audio signal, the time signal indicating a time of the output on the audio output device, and the patient control processor is configured to output an error signal if the time indication is not contemporaneous with the audio output from said audio output device within a predefined range of time. The audio output device includes a speaker. The pattern includes an audio sound power. The if the time indication is not contemporaneous with the audio output from said audio output device within said predefined range of time, then the patient control processor prevents use of a treatment machine. If the patient control processor detects an alarm condition during a treatment, it outputs an alarm signal to the user interface control processor for output to a speaker. If the time indication is not contemporaneous with the audio output from said audio output device within said predefined range of time, then the patient control processor outputs a data maintenance instruction to the user interface control processor to be output on a display. Implementations of the described techniques may include hardware, a method or process, or computer software on a computer-accessible medium.

One general aspect of the present disclosure includes a method for delivering treatment to a patient. The method also includes using a user interface control processor, receiving a test pattern from a patient control processor and outputting a responsive signal on an audio output device. The method also includes receiving audio, by a microphone positioned to receive audio output from said audio output device, and generating an audio signal that is interpretable by the patient control processor and which audio signal can be compared to a predefined pattern to determine whether it matches the pattern or not. The method also includes using the patient control processor outputting an error signal if the audio signal doesn't match the predefined pattern. Other embodiments of this aspect include corresponding computer systems, apparatus, and computer programs recorded on one or more computer storage devices, each configured to perform the actions of the methods.

Implementations may include one or more of the following features. The method where: using the user interface processor, generating a time indication in relation to the audio signal, the time signal indicating a time of the output on the audio output device, and the patient control processor is configured to output an error signal if the time indication is not contemporaneous with the audio output from said audio output device within a predefined range of time. The audio output device includes a speaker. The pattern includes an audio sound power. The pattern includes a time or frequency pattern with a range of frequencies with a distinctive audio signature. The if the time indication is not contemporaneous with the audio output from said audio output device within said predefined range of time, then, using the patient control processor, preventing a use of a treatment machine. If the patient control processor detects an alarm condition during a treatment, it outputs an alarm signal to the user interface control processor for output to a speaker. If the time indication is not contemporaneous with the audio output from said audio output device within said predefined range of time, then, using patient control processor outputting a data maintenance instruction to the user interface control processor to be output on a display. Implementations of the described techniques may include hardware, a method or process, or computer software on a computer-accessible medium.

One general aspect of the present disclosure includes a method for testing a treatment machine. The method also includes using a processor, generating a test pattern from the processor and outputting a responsive signal on an audio output device. The method also includes receiving audio, by a microphone positioned to receive audio output from said audio output device, and generating an audio signal that is interpretable the processor and which audio signal can be compared to a predefined pattern to determine whether it matches the pattern or not. The method also includes using the processor, outputting an error signal if the audio signal doesn't match the predefined pattern. Other embodiments of this aspect include corresponding computer systems, apparatus, and computer programs recorded on one or more computer storage devices, each configured to perform the actions of the methods.

Implementations may include one or more of the following features. The method where: using the processor, generating a time indication in relation to the audio signal, the time signal indicating a time of the output on the audio output device, and the patient control processor is configured to output an error signal if the time indication is not contemporaneous with the audio output from said audio output device within a predefined range of time, the audio output device includes a speaker, the pattern includes an audio sound power. If the patient control processor detects an alarm condition during a treatment, it outputs an alarm signal to the user interface control processor for output to a speaker. The if the time indication is not contemporaneous with the audio output from said audio output device within said predefined range of time, then, using the patient control processor, preventing a use of a treatment machine. The if the time indication is not contemporaneous with the audio output from said audio output device within said predefined range of time, then, using patient control processor outputting a data maintenance instruction to the processor to be output on a display. The pattern includes a time or frequency pattern with a range of frequencies with a distinctive audio signature. Implementations of the described techniques may include hardware, a method or process, or computer software on a computer-accessible medium.

It is, thus, apparent that there is provided, in accordance with the present disclosure, iterative testing of treatment event alarm delivery and the systems and devices responsible therefor. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A dialysis system for delivering a treatment to a patient, comprising:
 a dialyzer for conducting dialysis of a patient;
 a patient control processor;
 a user interface control processor configured to receive a test display pattern from the patient control processor and to output an image corresponding to the test display pattern on a graphical output device; and
 an optical sensor configured to capture a brightness and a test display pattern timing on the graphical output device, wherein
 the patient control processor is configured to output an error signal if the brightness and the test display pattern timing captured by the optical sensor does not match an expected brightness and test display pattern on the graphical output device.

2. The dialysis system of claim 1, wherein:
 the user interface control processor is configured to generate a time indication in relation to the test display pattern on the graphical output device, the time indication indicating a time of the output on the graphical output device, and the patient control processor is configured to output the error signal if the time indication is not contemporaneous with outputting of the image on the graphical output device within a predefined range of time.

3. The dialysis system of claim 2, wherein:
 the optical sensor includes an imaging device.

4. The dialysis system of claim 2, wherein the patient control processor is configured to prevent patient treatment with the dialysis system if the time indication is not contemporaneous with the outputting of the image on the graphical output device within said predefined range of time.

5. The dialysis system of claim 4, wherein:
 the patient control processor is configured to detect an alarm condition during the treatment, and in response to detecting the alarm condition to output an alarm signal to the user interface control processor for output to a speaker.

6. The dialysis system of claim 1, wherein the optical sensor is embedded within the graphical output device.

7. A method for delivering a treatment to a patient, comprising:
 using a user interface control processor to receive a test display pattern from a patient control processor used in a system for delivering a treatment for a patient to output an image corresponding to the test display pattern on a graphical display device;
 detecting the image displayed on the graphical display device by a camera with a view of the graphical display device, and generating a signal by the camera that is interpretable by the patient control processor; and,
 comparing the signal generated by the camera to templates to determine whether the image displayed on the graphical display device matches the templates or not;

wherein the patient control processor is configured to output an error signal in response to the signal generated by the camera not matching the templates.

8. The method of claim 7, further comprising:
wherein the user interface control processor is configured to generate a time indication in relation to the test display pattern, the time indication indicating a time of the output on the graphical display device and
configured to output the error signal if the time indication is not contemporaneous with the outputting of the image on the graphical display device within a predefined range of time.

9. The method of claim 8, wherein the patient control processor is configured for preventing delivering the treatment to the patient if the time indication is not contemporaneous with the outputting of the image on the graphical display device within said predefined range of time.

10. The method of claim 9, wherein the patient control processor is configured for outputting an alarm signal to the user interface control processor for output to a speaker if the patient control processor detects an alarm condition during the treatment.

\* \* \* \* \*